(12) United States Patent
Tu et al.

(10) Patent No.: US 10,216,983 B2
(45) Date of Patent: Feb. 26, 2019

(54) TECHNIQUES FOR ASSESSING GROUP LEVEL COGNITIVE STATES

(71) Applicant: General Electric Company, Schenectady, NY (US)

(72) Inventors: Peter Henry Tu, Niskayuna, NY (US); Tao Gao, Niskayuna, NY (US); Jilin Tu, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/370,736

(22) Filed: Dec. 6, 2016

(65) Prior Publication Data

US 2018/0157902 A1    Jun. 7, 2018

(51) Int. Cl.
| | |
|---|---|
| *G06K 9/00* | (2006.01) |
| *G06N 3/00* | (2006.01) |
| *G06K 9/62* | (2006.01) |
| *G06N 3/04* | (2006.01) |
| *A61B 5/00* | (2006.01) |
| *A61B 5/16* | (2006.01) |
| *G06N 99/00* | (2019.01) |
| *G06T 7/277* | (2017.01) |

(52) U.S. Cl.
CPC ........ *G06K 9/00335* (2013.01); *A61B 5/0013* (2013.01); *A61B 5/0022* (2013.01); *A61B 5/0077* (2013.01); *A61B 5/165* (2013.01); *A61B 5/742* (2013.01); *A61B 5/746* (2013.01); *A61B 5/747* (2013.01); *G06K 9/0055* (2013.01); *G06K 9/00281* (2013.01); *G06K 9/00302* (2013.01); *G06K 9/00778* (2013.01); *G06K 9/6277* (2013.01); *G06N 3/049* (2013.01); *G06N 99/005* (2013.01); *A61B 2576/00* (2013.01); *G06K 9/0061* (2013.01); *G06K 9/00718* (2013.01); *G06N 3/0445* (2013.01); *G06T 7/277* (2017.01)

(58) Field of Classification Search
CPC .................. G06N 99/005; G06N 7/005; G06T 2207/20084; G06K 9/00335; G06K 9/00523; G06K 9/00288
See application file for complete search history.

(56) References Cited

U.S. PATENT DOCUMENTS

| | | |
|---|---|---|
| 7,418,082 B2 | 8/2008 | Levene et al. |
| 7,450,683 B2 | 11/2008 | Tkaczyk et al. |

(Continued)

FOREIGN PATENT DOCUMENTS

| | | |
|---|---|---|
| CN | 103716324 A | 4/2014 |
| WO | 2008064431 A1 | 6/2008 |
| WO | 20080644431 A1 | 6/2008 |

OTHER PUBLICATIONS

Kang Hoon Lee, Myung Geol Choi, Qyoun Hong, and Jehee Lee. 2007. "Group behavior from video: a data-driven approach to crowd simulation." In Proceedings of the 2007 ACM SIGGRAPH/Eurographics symposium on Computer animation (SCA '07). Eurographics Association, Aire-la-Ville, Switzerland, Switzerland, 109-118.*

(Continued)

*Primary Examiner* — Utpal D Shah
(74) *Attorney, Agent, or Firm* — GE Global Patent Operation; Nitin Joshi

(57) ABSTRACT

A security monitoring technique includes receiving data related to one or more individuals from one or more cameras in an environment. Based on the input data from the cameras, agent-based simulators are executed that each operate to generate a model of behavior of a respective individual, wherein an output of each model is symbolic sequences representative of internal experiences of the respective individual during simulation. Based on the symbolic sequences, a subsequent behavior for each of the respective individuals is predicted when the symbolic sequences match a query symbolic sequence for a query behavior.

18 Claims, 9 Drawing Sheets

(56) References Cited

U.S. PATENT DOCUMENTS

| | | | |
|---|---|---|---|
| 7,486,764 | B2 | 2/2009 | Tkaczyk et al. |
| 8,442,839 | B2 | 5/2013 | Yen et al. |
| 2004/0057556 | A1 | 3/2004 | Luhta et al. |
| 2006/0059113 | A1 | 3/2006 | Kuznar et al. |
| 2006/0153328 | A1 | 7/2006 | Schlomka et al. |
| 2011/0263946 | A1 | 10/2011 | El et al. |
| 2012/0250982 | A1* | 10/2012 | Ito .................. G06T 7/0042 382/159 |
| 2012/0310591 | A1* | 12/2012 | Win .................. G01C 21/165 702/150 |
| 2013/0173504 | A1* | 7/2013 | Tu .................. G06N 99/005 706/12 |
| 2014/0222738 | A1 | 8/2014 | Joyce et al. |
| 2014/0355734 | A1 | 12/2014 | Ying |
| 2015/0179291 | A1 | 6/2015 | Yu |
| 2015/0282766 | A1* | 10/2015 | Cole .................. A61B 5/7267 702/139 |
| 2016/0124908 | A1 | 5/2016 | Cecchi et al. |
| 2016/0142679 | A1* | 5/2016 | Miyoshi .................. H04N 7/18 348/159 |
| 2017/0358154 | A1* | 12/2017 | Ishikawa .............. G07C 5/0808 |

OTHER PUBLICATIONS

Khan Z., Balch T., Dellaert F. (2004) "An MCMC-Based Particle Filter for Tracking Multiple Interacting Targets." In: Pajdla T., Matas J. (eds) Computer Vision—ECCV 2004. ECCV 2004. Lecture Notes in Computer Science, vol. 3024. Springer, Berlin, Heidelberg.*

Anti-Scatter X-Ray Collimators, Nuclear Fields, 2013.

Shikhaliev, Tilted Angle CZT Detector for Photon Counting/Energy weighting X-Ray and CT Imaging, IOPSCIENCE, Aug. 15, 2006.

Kappler et al., "CT at Elevated X-ray Tube Currents: Contrast Stability, Image Noise and Multi-Energy Performance", Medical Imaging 2014: Physics of Medical Imaging, Feb. 15, 2014.

Duric et al., "Integrating Perceptual and Cognitive Modeling for Adaptive and Intelligent Human-Computer Interaction", Proceedings of the IEEE, vol. 90, Issue 7, pp. 1272-1289, Jul. 2002.

Luo et al., "Agent-Based Human Behaviour Modeling for Crowd Simulation", Computer Animation and Virtual Worlds, vol. 19, Issue 3-4, pp. 271-281, Aug. 11, 2008.

Guo et al., "Face Verification using Large Feature Sets and One Shot Similarity," 978-1-4577-1359-0/11/$26.00 © 2011 IEEE.

Yang et al., "Discovering Motion Primitives for Unsupervised Grouping and One-Shot Learning of Human Actions, Gestures, and Expressions", IEEE Transactions on Pattern Analysis and Machine Intelligence, vol. 35, No. 7, Jul. 2013.

Chen, J., et al., "Bridging computer vision and social science: A multi-camera vision system for social interaction training analysis," IEEE International Conference on Image Processing (ICIP), pp. 823-826 (Sep. 27-30, 2015).

Cheng, X.E., et al., "3D tracking targets via kinematic model weighted particle filter," IEEE International Conference on Multimedia and Expo (ICME), pp. 1-6 (Jul. 11-15, 2016).

Gu, S., et al., "Neural Adaptive Sequential Monte Carlo," Cornell University Library, pp. 1-10 (Jun. 12, 2015).

Tu, P.H., "Surveillance and Social Situational Awareness," IEEE Advanced Video and Signal-based Surveillance, pp. 1-2 (2016) (Abstract).

Extended European Search Report and Opinion issued in connection with corresponding EP Application No. 17204871.2 dated May 8, 2018.

* cited by examiner

TECHNIQUES FOR ASSESSING GROUP LEVEL COGNITIVE STATES

BACKGROUND

The subject matter disclosed herein relates to agent based inference for understanding group level cognitive states.

Understanding individual or crowd level behavior is an important field of study and may lead to behavior detection. Detecting a person's behavior may enable crime reduction and/or enhanced security in various locations where crowds typically gather, such as airports, train stations, sporting arenas, movie theaters, and the like. It is now generally recognized that improved techniques to detect a behavior prior to a person carrying out that behavior is desirable.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the present disclosure. Indeed, the disclosed techniques may encompass a variety of forms that may be similar to or different from the embodiments set forth below.

In one embodiment, a method is provided that includes the steps of receiving data related to one or more individuals from one or more cameras in an environment; executing one or more agent-based simulators that each operate to generate a model of behavior of a respective individual, wherein an output of each model is symbolic sequences representative of internal experiences of the respective individual during simulation; and predicting a subsequent behavior for each of the respective individuals when the symbolic sequences match a query symbolic sequence for a query behavior.

In another embodiment, a tangible, non-transitory computer-readable media is provided. The tangible, non-transitory computer-readable media stores computer instructions that, when executed by one or more processors, cause the one or more processors to: receive data related to one or more individuals from one or more cameras in an environment; execute one or more agent based simulators that each model behavior of a respective individual and each output symbolic sequences representative of internal experiences of the respective individual during simulation; and predict a subsequent behavior for each of the respective individuals when the symbolic sequences match a query symbolic sequence for a query behavior.

In another embodiment, a system is provided. The system includes one or more cameras that capture data related to a behavior of one or more individuals in an environment; one or more computing devices comprising one or more processors that: receive the data related to the behavior of one or more individuals from one or more cameras in an environment; execute one or more agent based simulators that each model the behavior of a respective individual and each output symbolic sequences representative of internal experiences of the respective individual during simulation; and predict a subsequent behavior for each of the respective individuals when the symbolic sequences match a query symbolic sequence for a query behavior; and a display coupled to the one or more computing devices and configured to display an indication representative of the subsequent behavior.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements.

Embodiments of the present disclosure generally relate to an agent based inference framework for behavior recognition. In some embodiments, a social behavior recognition system may be used to synthesize a narrative that describes the evolution of a group level interaction. Possible cognitive states and transitions of each individual in the group level interaction may be modeled. Behavior recognition may be achieved as a form of classification. Further, machine learning methods (e.g., recurrent neural networks) may be used to estimate these latent variables based on observations and the narrative gleaned by the social behavior recognition system. As such, recognition may result in estimates of the cognitive states that would have resulted in such observations.

In particular, in some embodiments, the social behavior recognition system may use computer vision methods to capture large numbers of social cues, such as locations of individuals, gaze directions, facial expressions, body poses, gestures, and/or eye movements, among others. Additionally, forward agent based simulators may be generated that model internal cognitive states, as well as observable physical states. The agent based simulators may synthesize various interactions between multiple parties based on the cues captured. Further, in some embodiments, particle filters with machine learning techniques may execute thousands of the agent based simulators. The particle filters that are similar to the observed actions of a group of people may be propagated. The machine learning techniques may include training recurrent neural networks based on simulated data to recognize observed sequences. In this way, the social behavior recognition system may infer the internal states of the observed individuals and predict future likely behaviors based on the internal states.

Figure 1:
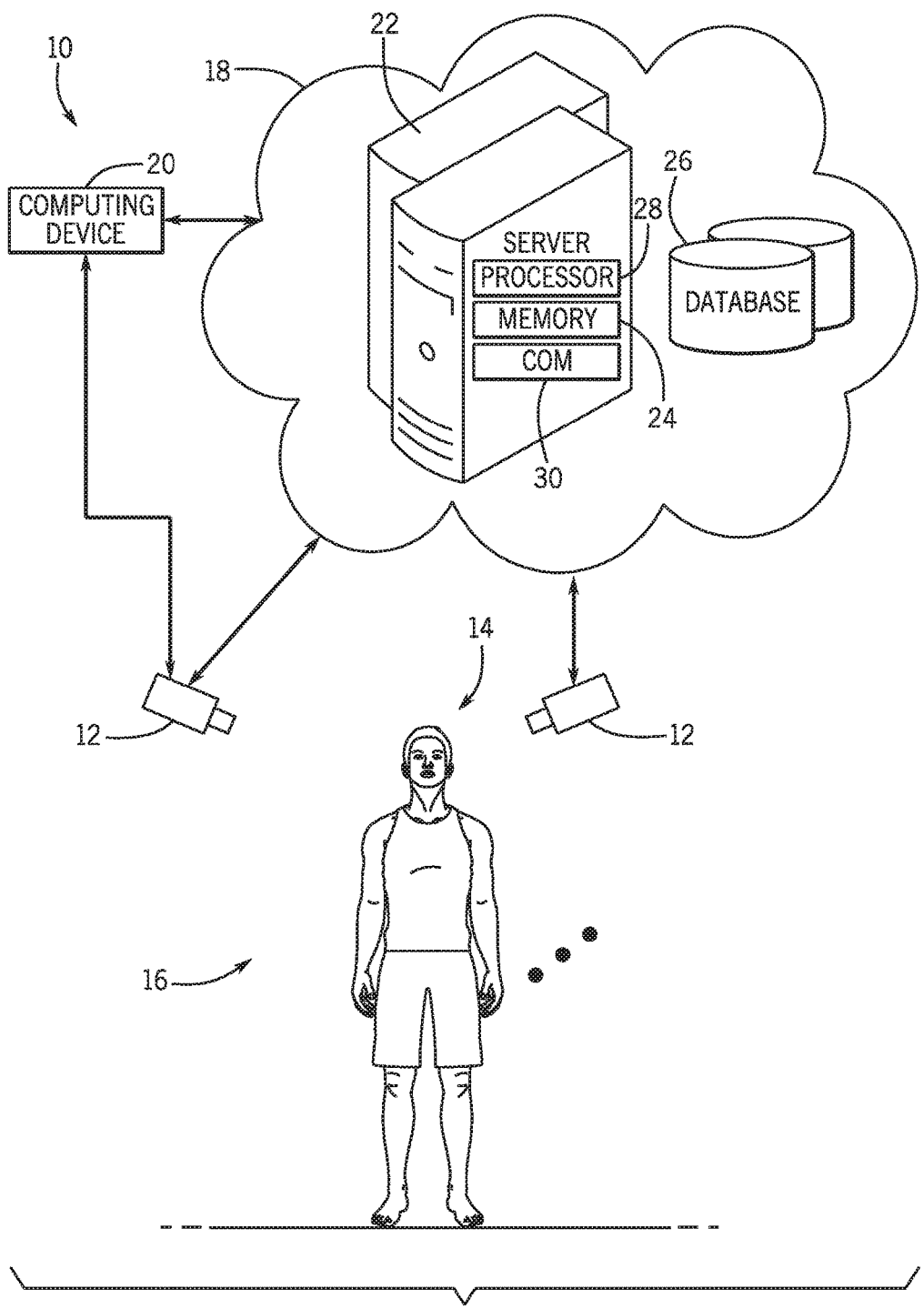
FIG. 1 is an illustration of a social behavior recognition system, in accordance with an embodiment.

With the foregoing in mind, FIG. 1 is an illustration of a social behavior recognition system 10, in accordance with an embodiment. The social recognition system 10 may consider a wide variety of visual cues, such as location of individuals, facial expression, gaze direction, body posture, body motion, and/or body gestures, among others. Based on the visual cues, the social recognition system 10 may estimate complex group level social states in a completely automated fashion. In some embodiments, the social behavior recognition system 10 may evaluate social interaction analysis as a latent variable inference problem. Further, in some embodiments, the social behavior recognition system 10 may include cameras 12 that capture data about multiple people 14 functioning freely in unconstrained environments 16. The social recognition system 10 may be used as the source of video analytic streams. As described more fully below, the social behavior recognition system 10 may be instantiated as a real-time, stand-off, (e.g., separate from the individuals) end-to-end social interaction analysis system.

As depicted, the social behavior recognition system 10 includes one or more cameras 12 enabled to capture still images, video, or both. The cameras 12 may be installed in any suitable location of the unconstrained environment 16, such as on a wall, ceiling, floor, or the like. The unconstrained environment 16 may include one or more people 14. For example, there may be a single individual person 14 present in the environment 16 or a crowd of people 14 may be present in the environment 16. The cameras 12 may be programmed or controlled to capture data related to the people 14. In some embodiments, the cameras 12 may be communicatively coupled to a cloud-based computing system 18 and/or a computing device 20. As such, the cameras 12 may transmit obtained data to the cloud-based computing system 18 and/or the computing device 20. The frequency of transmission may be periodically (e.g., every minute, 5 minutes, 30 minutes, 60 minutes, day, week, etc.) or streaming (e.g., continuous in real-time or near real-time). In some embodiments, the computing device 20 may be a smartphone, a smartwatch, a tablet, a laptop computer, a desktop computer, or the like.

The data obtained via the cameras 12 may be received by one or more servers 22 of the cloud-based computing system 18 and stored in one or more memories 24 of the servers 22 or in one or more databases 26 included in the cloud-based computing system 18 that are external to the servers 22. The servers 22 may be communicatively coupled to each other and may distribute various tasks between each other to perform the tasks more efficiently. The servers 22 may also include one or more processors 28 and a communication component 30. The communication component 30 may be a wireless or wired communication component that may facilitate communication between the cloud-based computing system 18, the cameras 12, and/or the computing device 20.

The processor 28 may be any type of computer processor or microprocessor capable of executing computer-executable code. The processor 28 may also include multiple processors that may perform the operations described below. The memory 24 may be any suitable articles of manufacture that can serve as non-transitory media to store processor-executable code, data, analysis of the data, or the like. These articles of manufacture may represent computer-readable media (e.g., any suitable form of memory or storage) that may store the processor-executable code used by the processor 28 to perform the presently disclosed techniques. Generally, the processor 28 may recognize behavior based on data obtained via the cameras 12, as described in detail below. Due to the distributed nature of the servers 22 in the cloud-based computing system 18, the shared resources of the servers 22 enable parallel processing to enable real-time feedback. For example, each server 22 may be responsible for processing a different portion of the data at substantially the same time and the results may be collected by a single server 22 that combines the results and outputs the results to the computing device 20. In this way, no one server 22 is inundated with a computationally expensive task and the processing time may be reduced.

The databases 26 may store the image and/or video data captured by the cameras 12. Also, the databases 26 may store other information, such as cognitive models including recurrent neural networks and particle filters that are determined to be sufficiently accurate in recognizing behaviors. Further, the databases 26 and/or the memory 24 may store historical video and/or image data obtained by the cameras 12.

The computing device 20 may store an application that provides a graphical user interface (GUI) that displays whether a certain behavior of one or more people 14 is detected, as well as any relevant information related to the people 14 and/or actions (e.g., call emergency services, sound alarm, trigger alert, send message, display alert, etc.) to be taken. That is, in some embodiments, the application may not perform any processing, such as methods for recognizing behavior. Instead, in some embodiments, the application may just function as a front-end display of data and results of the behavior recognition techniques performed by the cloud-based computing system 18. For example, in a client-server architecture, a website may be accessed via a browser on the computing device 20 and the website may function as a thin-client in that it just displays information provided by the cloud-based computing system 18 without actually performing any modeling. However, in some embodiments, the application stored on the computing device 20 may receive the data from the cameras 12 and perform the behavior recognition techniques disclosed herein.

Although the components described above have been discussed with regard to the servers 22 of the cloud-based computing system 18, it should be noted that similar components may make up the computing device 20. Further, it should be noted that the listed components are provided as example components and the embodiments described herein are not to be limited to the components described with reference to FIG. 1.

The cameras 12 may include fixed red, green, blue, and depth (RGB+D) cameras, which produce estimates of location and articulated body motion. Also, the cameras 12 may include pan-tilt-zoom (PTZ) cameras that may be tasked based on such tracking results to capture high resolution facial imagery. Facial landmark fitting and tracking is performed so as to extract facial expressions and gaze directions. The social behavior recognition system 10 may distill a stream of person specific cues into a set of site-level aggregate statistics which are independent of the configuration and number of observed individuals. Such measures may include emotional affect (derived from observed facial expressions), proximity (derived from tracked positions), activity motion (derived from motions), and engagement (derived from position and gaze direction). The social behavior recognition system 10 may continuously generate these statistics resulting in a time-series representation of the statistics. Sets of graphical models may be used by the cloud-based computing system 18 and/or the computing device 20 to process these measures, thereby resulting in a continuous estimate of various group-level social states such as rapport and hostility.

It should be noted that the social behavior recognition system 10 may include a modular design for its system architecture. In some embodiments, components of the social behavior recognition system 10 may consume inputs such as raw video feeds from the cameras 12 and metadata generated by other modules. In turn, each module may generate metadata that is inserted into a message-passing publish and subscribe architecture. Using multiple computing platforms, the real-time social behavior recognition system 10 may include multi-camera tracking, PTZ control, facial analysis, data-consolidation, and social-state inference. This type of modular design may enable the incorporation of multiple third party capabilities into the social behavior recognition system 10.

One or more processors of the cloud-based computing system 18 and/or the computing device 20 may execute various modules that are implemented as computer instructions. The modules may include a tracking module, an articulated motion analysis module, a PTZ camera control module, a facial analysis module, and/or an inference module.

Starting with the tracking module, a detect-and-track paradigm may be used to estimate the location and trajectory of each subject (e.g., people 14) that are located in a specific region of interest (e.g., environment 16). Multiple RGB+D cameras 12 may be initially calibrated with respect to a world coordinate system. Imagery from each camera 12 may be used to independently generate a set of person detections and associated appearance signatures. These detections may be matched to existing trackers. Detections that are not associated with an existing tracker may be used to initialize a new tracker. Trackers that persistently fail to be associated with new detections may be terminated.

In addition, the cloud-based computing system 18 and/or the computing device 20 may execute the articulated motion analysis module. In addition to tracking, the RGB+D camera imagery may be used to extract motion cues referred to as "space-time-corners". These cues may be associated with a spatial histogram defined based on the measured location and height of each subject. These spatial/frequency distributions may be used as a representation of articulated motion body based on RGB imagery captured with the PTC cameras 12.

Regarding the PTZ camera control module, the location of each PTZ camera 12 may be initially measured with respect to the world coordinate system. A calibration procedure may be used to map pan (P), tilt (T), and zoom (Z) values to (X, Y, Z) coordinates in the world coordinate system such that if a face is located at (X, Y, Z) then the resulting imagery from the PTZ camera 12 may enable various forms of facial analysis. The tracking module may generate the location of each person in ground plane coordinates (X, Y). The Z value may be determined based on an estimate of subject height. An optimization algorithm may be used to automatically assign PTZ cameras 12 to tracked subjects.

Regarding the facial analysis module, given high resolution imagery generated by the PTZ cameras 12, the following operations may be performed: (1) face detectors are used to produce a bounding box of the subject's face, (2) eye detectors are used to locate the subject's eyes, (3) if both eyes are detected, a facial landmark model is fitted to the subject's face, (4) an estimate of the vertical and horizontal gaze directions may be computed based on the shape of the fitted landmark model, (5) an estimate of the horizontal eyeball location is computed allowing for detection of events such as "averted gaze", (6) the fitted landmark model may be used to synthesize a frontal view of the subject's face, and (7) gross facial expression models may be used to estimate a set of common facial expressions.

Regarding the inference module, given a stream of metadata associated with each person 14 (e.g., location, articulated motion, gaze direction, facial expression) a set of aggregate social signals may be generated. For the purposes of inferring group level social concepts such as rapport and hostility, graphical models may be used to reason over the aggregate social signals resulting in real-time estimates of the probability distribution associated with each social concept.

Figure 2:
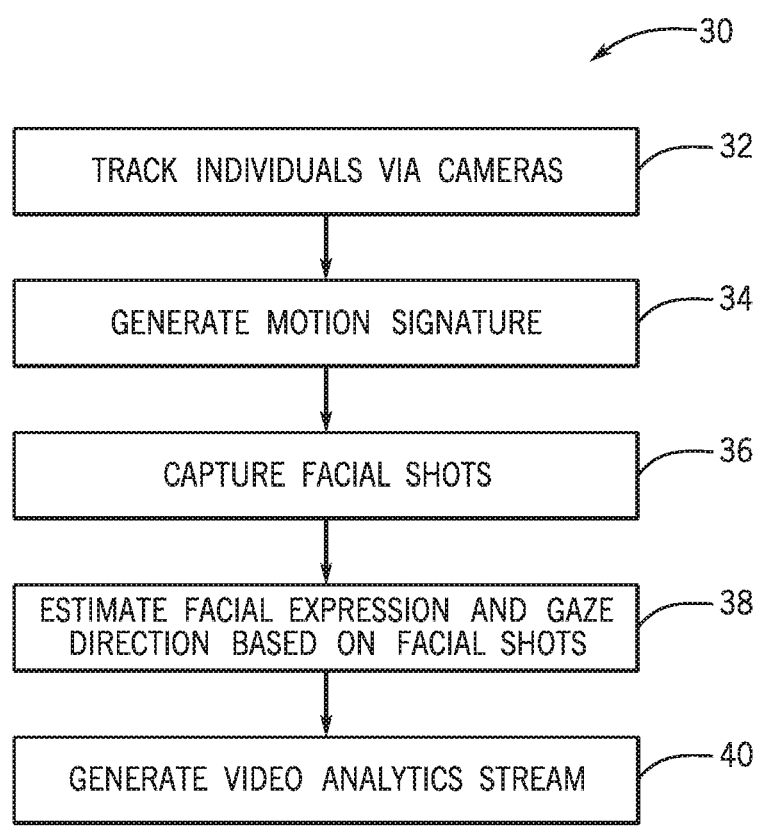
FIG. 2 is a flow diagram of a process suitable for generating a video analytics stream, in accordance with an embodiment.

FIG. 2 is a flow diagram of a process 30 suitable for generating a video analytics stream, in accordance with an embodiment. Although the following description of the process 30 is described with reference to the processor 28 of one or more servers 22 of the cloud-based computing system 18, it should be noted that the process 30 may be performed by one or more other processors disposed on other devices that may be capable of communicating with the cameras 12 and/or the cloud-based computing system 18, such as the computing device 20, or other components associated with the social behavior recognition system 10. Additionally, although the following process 30 describes a number of operations that may be performed, it should be noted that the process 30 may be performed in a variety of suitable orders and all of the operations may not be performed. It should be appreciated that the process 30 may be distributed between the servers 20 of the cloud-based computing system 18. It should be noted that various modules (e.g., tracking, articulated motion analysis, PTZ camera control, facial analysis, and/or inference) may be used to perform the process 30.

Referring now to the process 30, the processor 28 may track (block 32) individuals 14 via the PTZ cameras 12 in the environment 16. The processor 28 may also generate (block 34) a motion signature for each individual 14 based on space-time interest points. The processor 28 may also capture (block 36) high-resolution facial images by controlling the PTZ cameras 12. Also, the processor 28 may estimate (block 38) facial expression and gaze direction based on the facial images. The processor 28 may then generate (block 40) a video analytics stream. For each frame, the video analytics stream may be composed of a set of person descriptors which encode: (1) location in site coordinates, (2) a motion-signature, (3) an expression profile (joy, fear, surprise, frustration, anger), and (4) gaze direction (vertical and horizontal). In addition, each individual 14 may be linked to a prior person observation via a track ID, which may enable temporal analysis.

Figure 3:
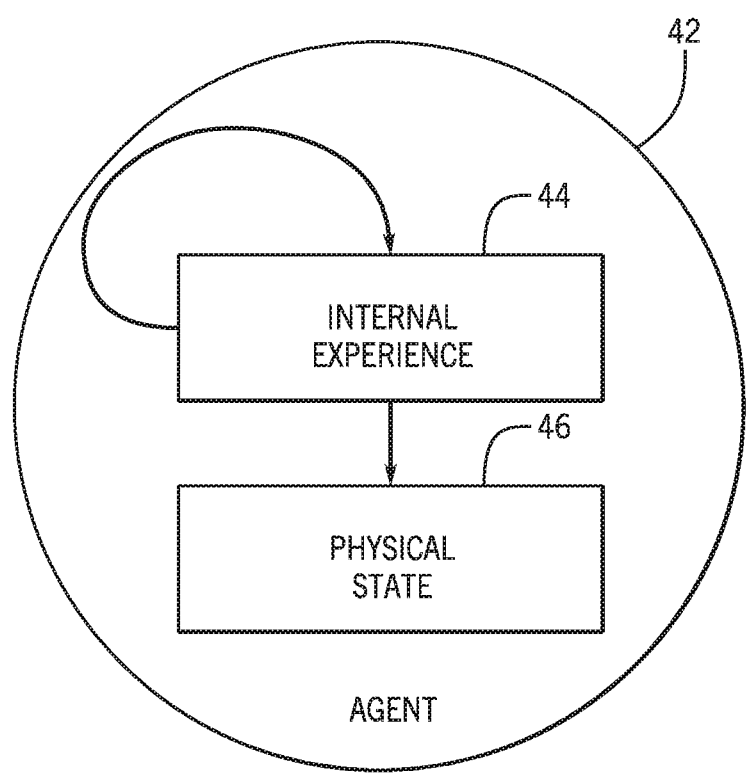
FIG. 3 is a block diagram of an individual represented as an agent with an internal experience and a physical state, in accordance with an embodiment.

Using the video analytics stream, the cloud-based computing system 18 and/or the computing device 20 may perform agent based inference techniques to determine whether a certain behavior is recognized. The observation of cues included in the video analytics stream may enable analysis of group level interaction. Further, the cues may be used to characterize the physical states of individuals 14 participating in group level behaviors. Such individuals 14 may be modeled as cognitive agents 42 that are in possession of a subjective form of internal experience 44, as depicted in FIG. 3.

Models for these internal experiences 44 may include concepts such as emotions, intentions, goals, plans, expectations, representations of other individuals 14, and so forth. Each individual 14 may be viewed as an agent 44 where each agent 44 has a physical state 46 that is observable (e.g., by the cameras 12) and a latent internal experience 44 (internal state) that is not open to direct observation. The physical state 46 may include relative position of the agent 42, gaze angles, expressions, gestures, affective pose, and/or speech. Additionally, as depicted, the internal experience 44 drives the physical state 46.

Figure 4:
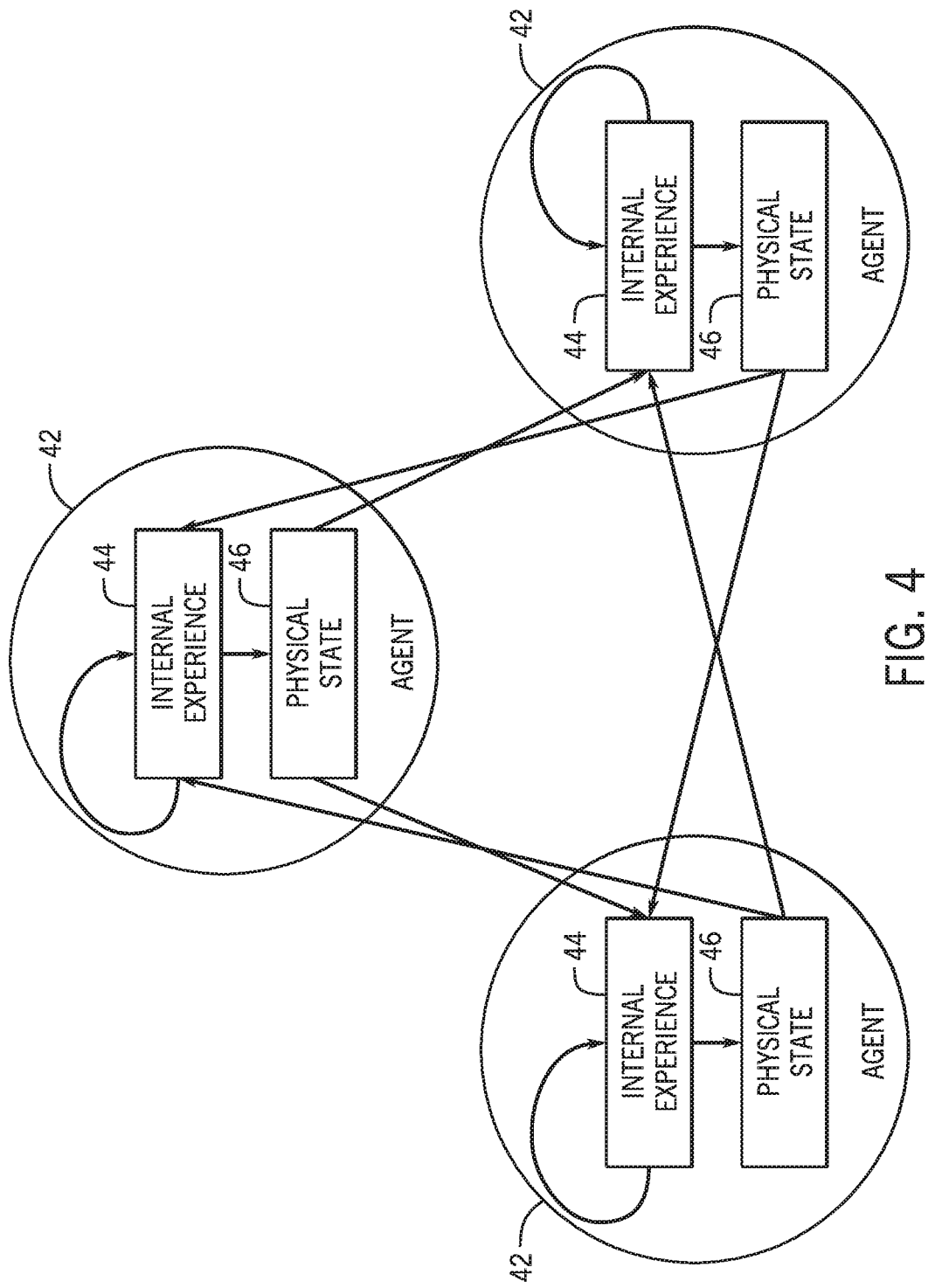
FIG. 4 is a block diagram of relationships between numerous agents, in accordance with an embodiment.
Figure 5:
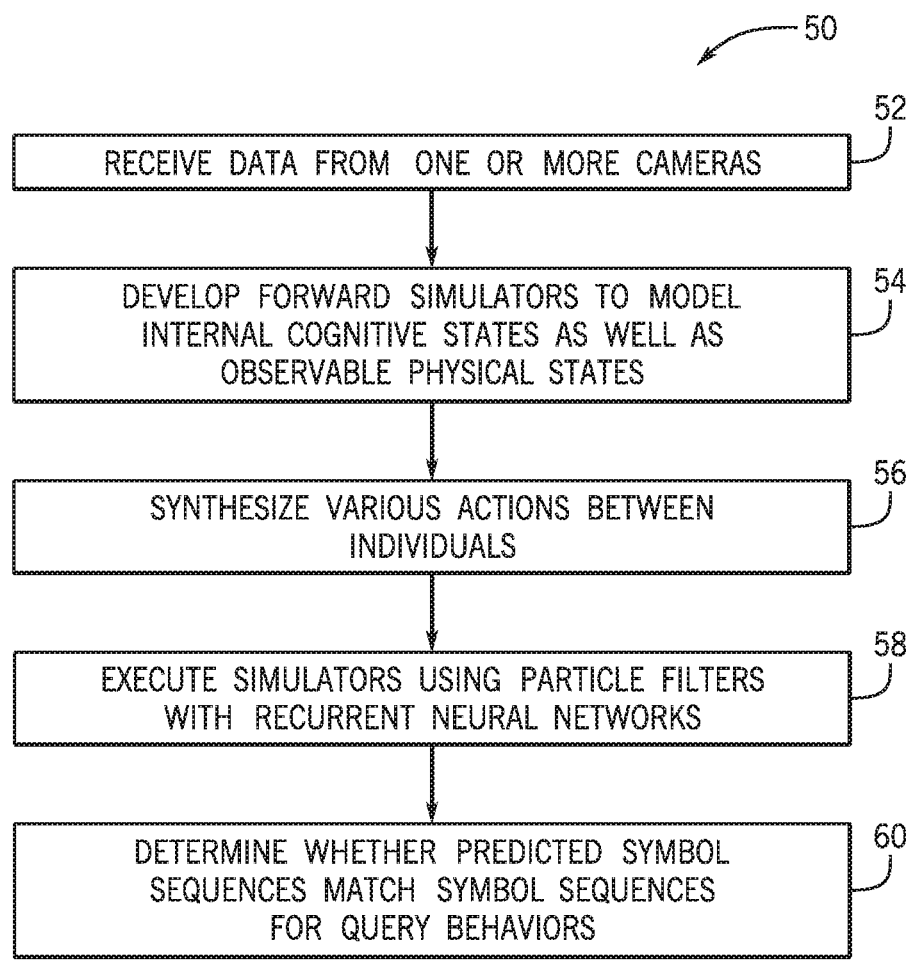
FIG. 5 is a flow diagram of a process suitable for detecting behavior via agent based inference, in accordance with an embodiment.

Future internal experiences 44 may be based on the current internal experience 44, as well as observations of the physical state 46 of third party agents 42. For example, FIG. 4 depicts these relationships between three interacting agents 42, each with their own internal experiences 44 and physical states 46. From an analysis perspective, the physical state 46 of each agent may be directly observed, while the internal experiences 46 may be inferred.

If, based on observations of the physical states 46, estimates of the internal experiences 44 of each agent 42 are made, a much richer form of behavior recognition may emerge. However, due to the non-linear and stochastic nature of these processes, it will not be possible to compute such latent variables via direct inversion of the observations. Thus, inference strategies based on the ability to model and hence forward simulate agent based behavior are used in certain embodiments of the present disclosure.

Given a sequence of observed physical states 46 of a group of interacting individuals 14 (e.g., agents 42), some embodiments may infer the corresponding sequence of latent internal experiences 44. The latent internal experiences 44 and observable physical states 46 may be characterized by a set of symbols. As such, some embodiments, may derive a full sequence of interlaced latent and observed symbols given an observed symbol sequence. By modeling the mechanisms associated with the internal experiences 44, agent based simulators may be used to synthesize complete latent/observable behavior sequences. A vast set of such synthetic sequences may then be produced via random sampling methods. Some embodiments of agent based simulation may use two types of inference strategies: "Hypothesis and Test" and "Recognition via Machine Learning".

The hypothesize and test approach may be based on the idea of (1) synthesizing a large number of possible behavior sequences, (2) developing a similarity measure/likelihood function that compares any two sequences based on physical symbols alone, and (3) estimating the latent symbols of the query sequence based on the latent symbols of the most similar synthetic sequence. Due to the vast set of synthetic sequences, some embodiments may employ "Multiple Hypotheses Tracking (MHT)" as a suitable form of inference. In particular, as discussed below, some embodiments may use a particle filtering framework. For example, similar to particle filtering methods, other techniques such as Markov Chain Monte Carlo (MCMC) and Gibbs sampling may be used.

A flow diagram of a process 50 suitable for detecting behavior via agent based inference is depicted in FIG. 3, in accordance with an embodiment. Although the following description of the process 50 is described with reference to the processor 28 of one or more servers 22 of the cloud-based computing system 18, it should be noted that the process 50 may be performed by one or more other processors disposed on other devices that may be capable of communicating with the cameras 12 and/or the cloud-based computing system 18, such as the computing device 20, or other components associated with the social behavior recognition system 10. Additionally, although the following process 50 describes a number of operations that may be performed, it should be noted that the process 50 may be performed in a variety of suitable orders and all of the operations may not be performed. It should be appreciated that, in some embodiments, the process 50 may be distributed between the servers 22 of the cloud-based computing system 18 and the computing device 20.

Referring now to the process 50, the processor 28 may receive (block 52) data from one or more cameras 12. The data may enable generation of the video analytic stream that includes various cues, such as location of individuals, facial expression, gaze direction, body posture, body motion, and/or body gestures, among others. The processor 28 may also develop (block 54) forward agent simulators to model internal emotions 44 (cognitive states) as well as observable physical states 46 based on the data. Several equations may be used to model the agent simulators. For example, the following equations may be used:

$$e_{i,t} = f_e(e_{i,t-1}, \{E_{j \neq i, t-1}\}, c_i) \qquad \text{(Equation 1)}$$

$$E_{i,t} = f_E(e_{i,t}, c_i) \qquad \text{(Equation 2)}$$

$$X_{i,t} = f_X(\{X_{j,t-1}\}, c_i) \qquad \text{(Equation 3)}$$

Where $e_{i,t}$ is the emotional state of agent i at time t (hidden), $E_{i,t}$ is the observed expression of agent i at time t (observable), $X_{i,t}$ is the location and gaze direction of agent i at time t (observable), and $c_i$ is the character type of agent i (hidden).

The processor 28 may also synthesize (block 56) various actions between individuals 14. Also, the processor 28 may execute (block 58) the agent simulators using particle filters with recurrent neural networks. Particle filtering may refer to an iterative process that attempts to estimate the temporal evolution of a set of latent state variables (e.g., internal experiences 44) given an observation sequence (e.g., cues derived from observed physical states 46). In particular, at time zero, an initial set of particles may be randomly instantiated. Each particle may consist of an estimate of the initial latent variable values and a prediction of the associated observable variables. The likelihood of each particle may be computed based on the similarity of the predicted and observed physical states 46. Sampling methods may be used to nominate particles for propagation to the next iteration based on these likelihood measures. Particle propagation may be based on stochastic sampling. In this way, particles that are able to track the observation sequence are allowed to persist. Particles that fail to predict the observed behavior are subsequently culled. The output is thus the most likely interpretations of the query sequence.

Particle filtering is a form of search that is reliant on accurate modeling of system dynamics resulting in accurate proposal distributions. Because the internal experience models may increase in complexity as they evolve, the use of recognition methods as a mechanism for guiding the evolution of the particle filters may be beneficial and used by some embodiments of the present disclosure. To this end, recurrent neural networks (RNNs) may be used.

RNNs may be viewed as a form of symbolic sequence recognition. For the purposes of illustration, consider the entire works of William Shakespeare. Each word can be represented by a unique symbol. Each sentence can then be viewed as a symbolic sequence. The corpus of Shakespearean plays thus becomes training data. Once an RNN has been trained, it can be given an initial seed sequence with as few as a single symbol. The RNN then produces a probability distribution for the next element in the sequence. Sampling methods can then be used to select the next element. This process can be repeated multiple times resulting in the synthesis of complete sequence that appear to resemble the properties of the training data. For example, given an initial seed of "The dog", a Shakespearian RNN might produce the following sentence: "The Dog cometh from yonder castle".

Accordingly, some embodiments may include using agent based simulators to construct a corpus of training data needed for construction of a behavior RNN that is capable of providing a behavior prediction or of characterizing observed behavior. Further, stochastic sampling on appropriately trained RNNs will be incorporated into the particle filtering framework. Instead of each particle having its own generative internal experience models, the particle will have a RNN. The particle RNNs may initially be seeded with random internal symbols. The particle RNNs may then predict through sampling the next set of physical symbols. These predicted physical symbols may be compared with the physical symbols of the query sequence. Likely particles may be allowed to transition to the next iteration. In this case, transitioning may involve predicting the next set of internal symbols.

As may be appreciated, while there are a potentially vast number of possible behavior sequences, by and large, the majority of sequences that may be encountered can be associated with a relatively small number of behavior modes. This is similar to the statement: "There are an infinite number of possible movies, however there are only 12 different types of movies". As such, given appropriate training data, knowledge associated with such modes may be encapsulated by the RNNs. Success of this inference paradigm is predicated on the ability to produce high fidelity cognitive agent based simulators.

The processor 28 may also determine (block 60) whether predicted symbol sequences match another symbol sequence for a query behavior. That is, the processor 28 may run simulations of the particle filters with RNNs to predict when the next set of internal symbols match internal symbols and/or physical symbols of a query behavior. When there is a match, the processor 28 may perform an action, such as calling emergency services, sounding an alarm, triggering an alert, displaying a message, sending a message, or the like.

Figure 6:
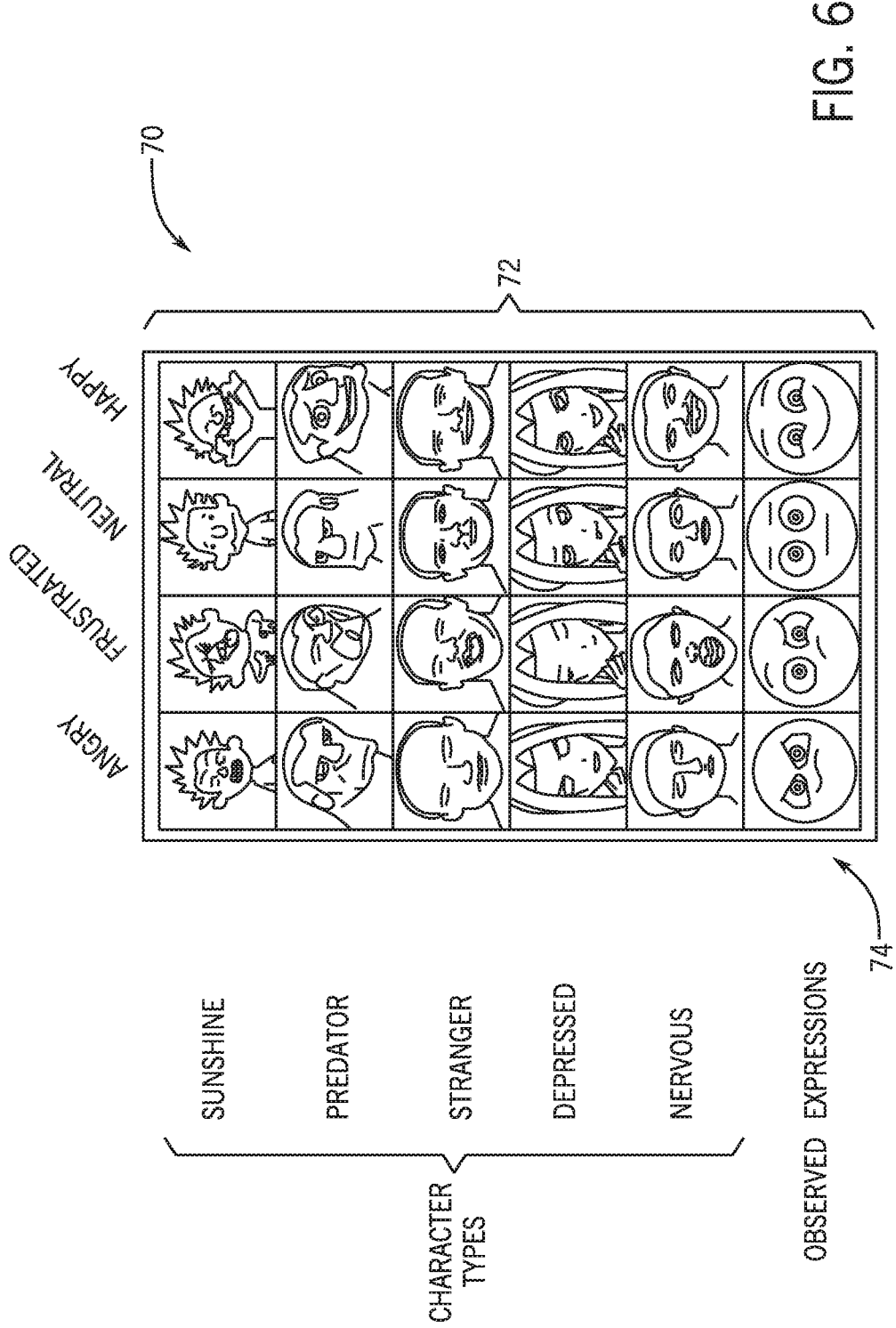
FIG. 6 is a chart including character emotions and expressions included in the agent based simulators, in accordance with an embodiment.

FIG. 6 is a chart 70 including character emotions and expressions included in the agent based simulators, in accordance with an embodiment. The character types may include sunshine, predator, stranger, depressed, and/or nervous. Each character type may be programmed to exhibit certain behaviors. For example, a sunshine character type may cause the agent to move to the center of a group of people in a simulation, a predator character type may cause the agent to get closer to the nearest agent in a simulation, a stranger character type may cause an agent to walk away from other agents, a depressed character type may cause the agent to move slowly, and a nervous character type may cause an agent to seek open spaces. The emotions may include angry, frustrated, neural, and/or happy. Further, observed expressions 74 may include a representation of a face with the associated expression mimicked. As depicted, various symbols 72 have been associated with each character type and emotion in the chart 70. Also, symbols for observed expression 74 have also been generated.

Figure 7:
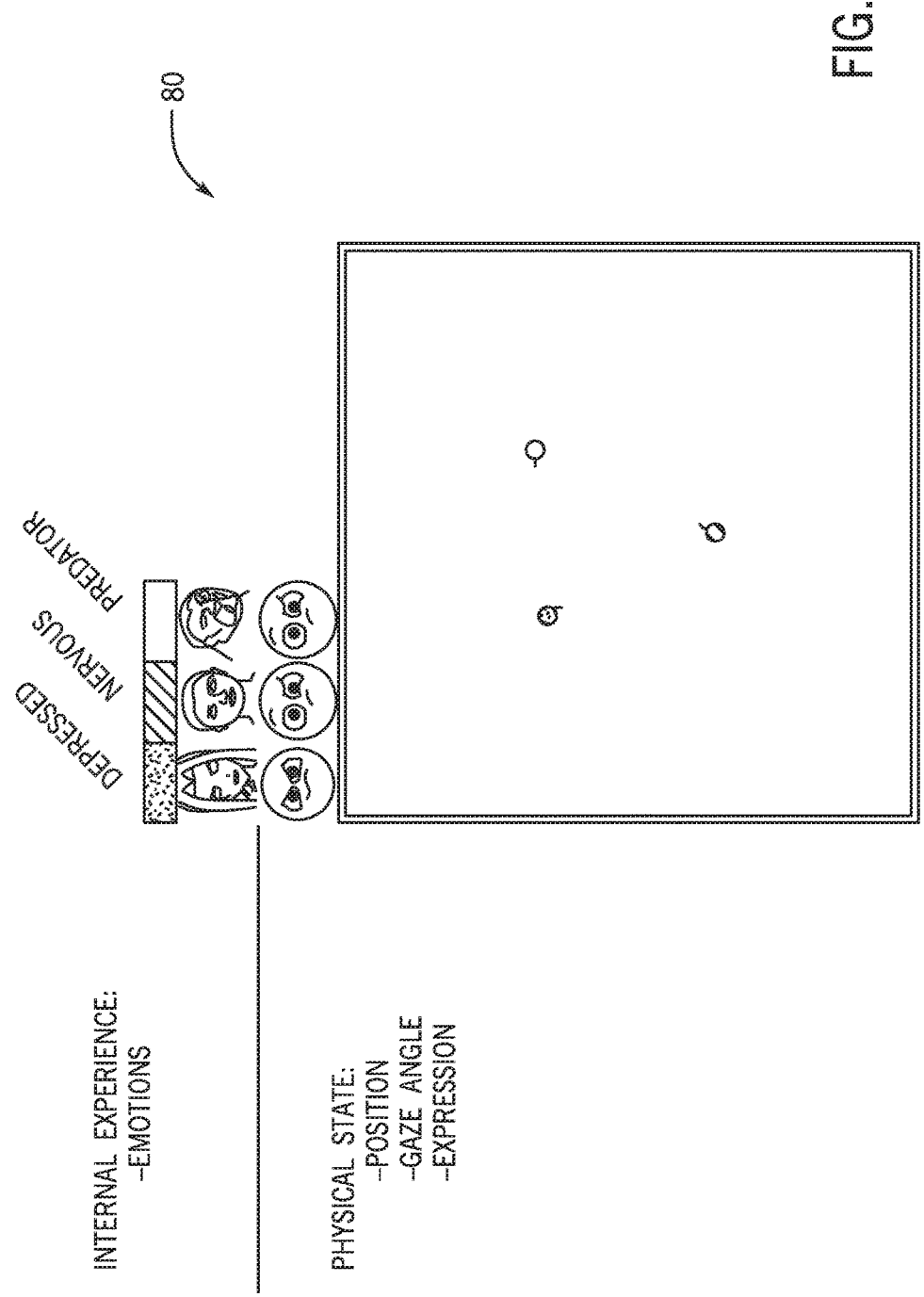
FIG. 7 is a view of simulated agents and their interactions, in accordance with an embodiment.

FIG. 7 is a view 80 of simulated agents and their interactions, in accordance with an embodiment. As depicted, the simulated agents may be color-coded to correspond with their character type (e.g., predator, nervous, and depressed). The agents may be programmed as noted above and the simulation may provide data on sequences of behavior in the group setting. The agents may include internal experiences 44 (emotions) and physical states 46 (position, gaze angle, and/or expression). As previously discussed, the physical states 46 are directly observable via the cameras 12, whereas the internal experiences 44 are hidden and may be inferred by the social behavior recognition system 10.

Figure 8:
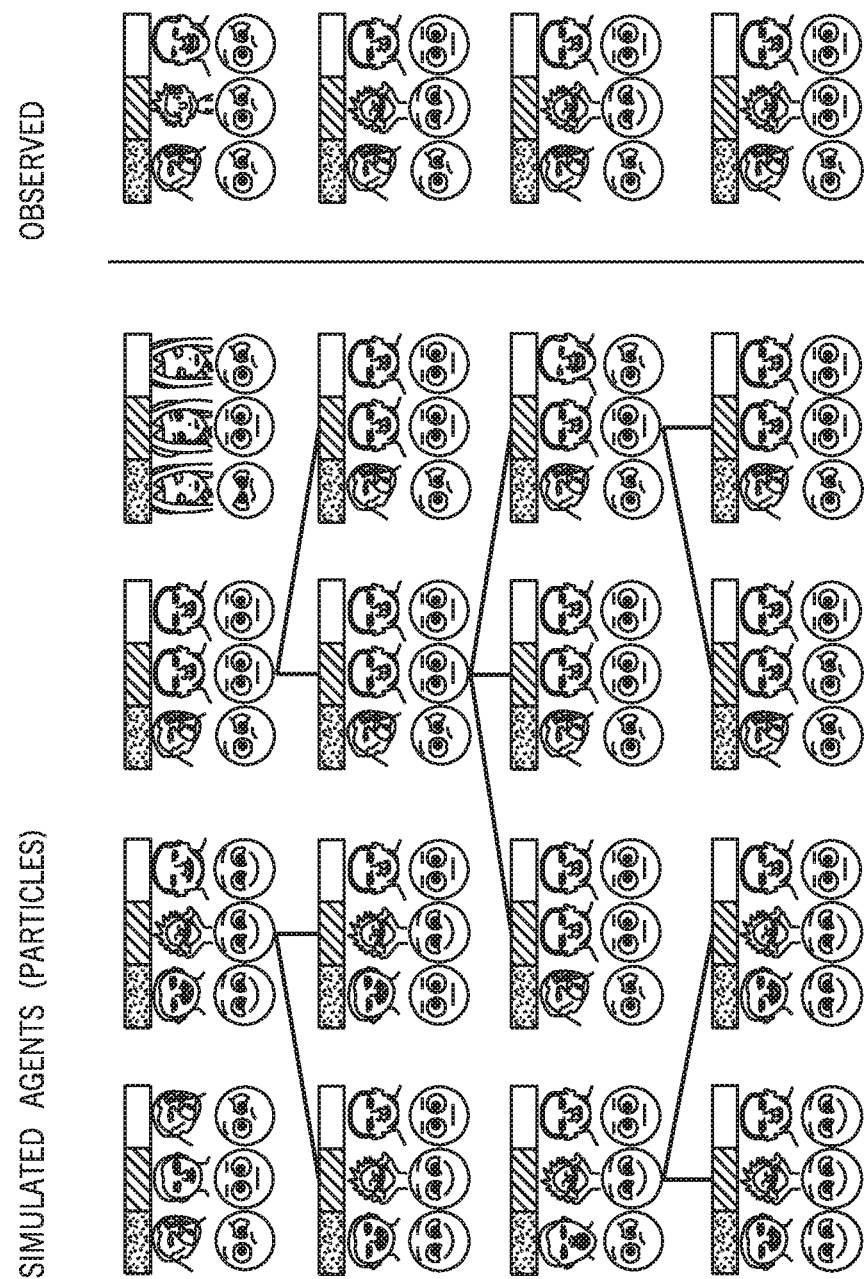
FIG. 8 is an example of particle filtering using simulated agents estimated from observed behavior, in accordance with an embodiment.

FIG. 8 is an example of particle filtering using simulated agents estimated from observed behavior, in accordance with an embodiment. As noted above, particle filtering may be an iterative process that attempts to estimate the temporal evolution of a set of latent variables (e.g., internal experiences 44 such as emotions) given an observation sequence. As such, the depicted simulated agents (particles) may be used to estimate the sequence of latent variable symbols based on the corresponding observed sequence for character type and expression symbols. In some embodiments, the particle filters include recurrent neural networks and the particle filters that successfully predict sequences of symbols (character type and/or emotion) are kept and particle filters that are unsuccessful are weeded out (e.g., terminated).

Figure 9:
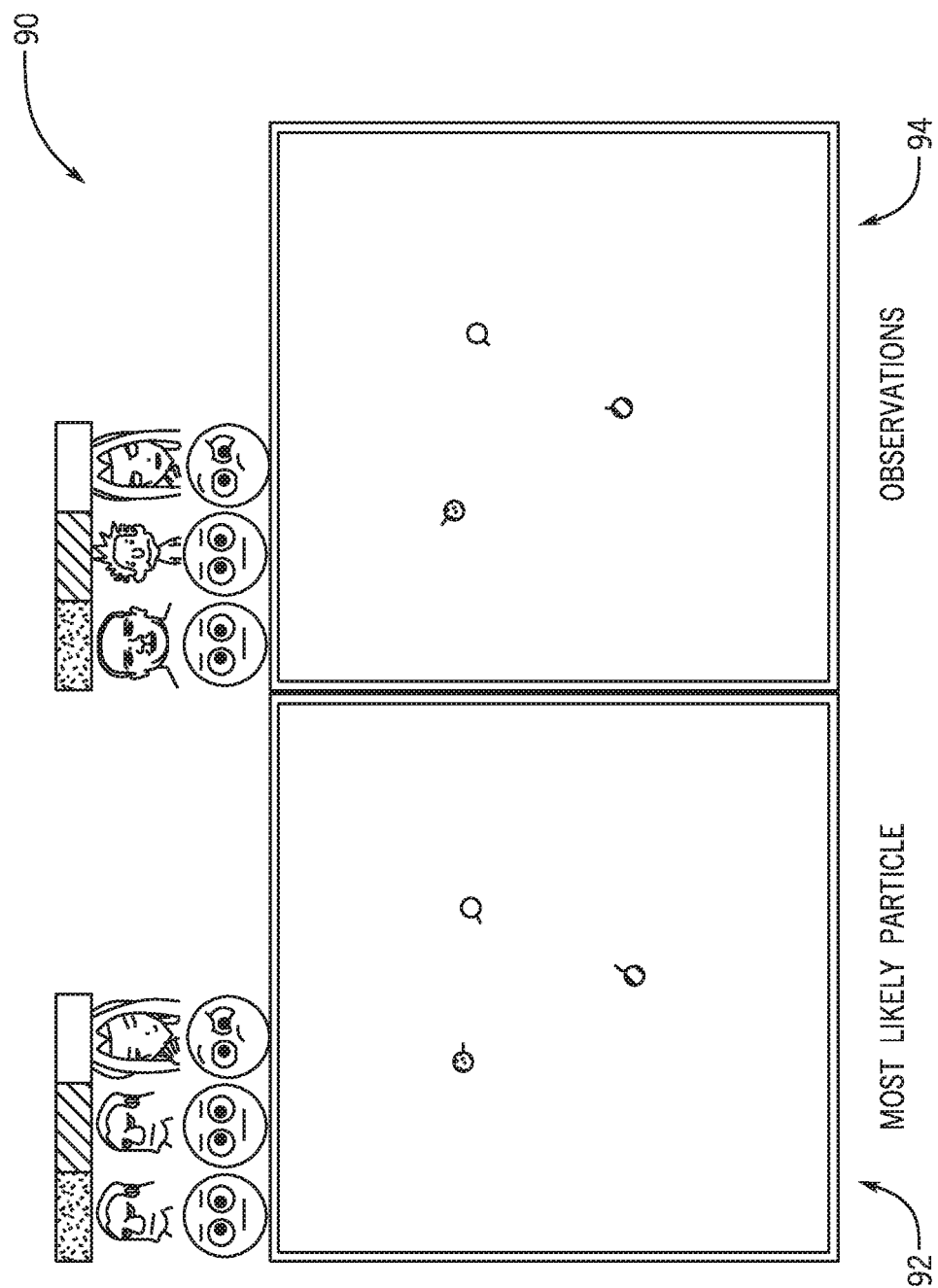
FIG. 9 is a view of a most likely particle selected as a result of executing simulated agents with particle filtering using recurrent neural networks, in accordance with an embodiment.

FIG. 9 is a view 90 of a most likely particle 92 selected as a result of executing simulated agents with particle filtering using recurrent neural networks, in accordance with an embodiment. The most likely particle 92 may be allowed to continue to execute to generate the full sequence of behavior symbols, thereby enabling prediction of subsequent actions. As described above, the observations may be based on data obtained via the cameras 12.

Technical effects of the invention include instantiating an agent based inference framework for behavior recognition. Behavior recognition may be useful in security monitoring. Although human behavior is complex, certain behavior patterns capable of being captured by cameras and identified by the present techniques may be flagged for review or action. Further, in one embodiment, the use of multiple recurrent neural networks may permit more efficient and streamlined computer performance relative to other video-based behavior assessment as only certain neural networks are propagated and others are terminated based on performance.

Embodiments enable behavior recognition as a form of classification using generative models to construct observable cues based on cognitive models. Thus, behavior recognition results in estimates of the cognitive states that would have resulted in such observations. Agent based simulators may be used to construct a corpus of training data used for construction of a behavior recurrent neural network. Stochastic sampling on appropriately trained recurrent neural networks may be incorporated into a particle filtering framework. Instead of each particle having its own generative internal experience models, the particles include a recurrent neural network. The particle recurrent neural networks may initially be seeded with random internal symbols. The particle recurrent neural networks may then predict through sampling the next set of physical symbols. These predicted physical symbols may be compared with the physical symbols of the query sequence. Likely particles may be allowed to transition to the next iteration. Transitioning may involve predicting the next set of internal symbols. The social behavior recognition system 10 may use various cameras 12 that are not borne by any individuals (e.g., located remote from the people 14). The cameras 12 may be used to capture and analyze non-verbal cues (e.g., emotional affect, proximity, activity/motion, engagement) of persons 14 in crowd/group level interactions.

This written description uses examples to disclose the embodiments, including the best mode, and also to enable any person skilled in the art to practice the disclosed subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
receiving data related to one or more individuals from one or more cameras in an environment;
executing one or more agent-based simulators that each operate to generate a model of behavior of a respective individual, wherein an output of each model is symbolic sequences representative of internal experiences of the respective individual during simulation; and
predicting a subsequent behavior for each of the respective individuals when the symbolic sequences match a query symbolic sequence for a query behavior;
wherein each model uses particle filtering and each particle includes recurrent neural networks that iteratively estimates temporal evolution of the symbolic sequences based on the data.

2. The method of claim 1, wherein particles that include similar symbolic sequences are allowed to transition to the next iteration to predict a next set of internal symbols of the symbolic sequences.

3. The method of claim 1, wherein particles that do not include similar symbolic sequences are terminated.

4. The method of claim 1, wherein the recurrent neural networks are used to predict the subsequent behavior based on the symbolic sequences.

5. The method of claim 4, wherein the recurrent neural networks are seeded with random internal experience symbols initially.

6. The method of claim 5, wherein the recurrent neural networks predict the subsequent behavior by sampling a next set of physical state symbols and comparing the next set of physical symbols to physical state symbols of the query symbolic sequence.

7. The method of claim 1, wherein the symbolic sequences include stored graphics for character type, emotion, observed expressions, or some combination thereof.

8. The method of claim 7, wherein the character type comprises sunshine, predator, stranger, depressed, or nervous, and the emotion comprises angry, frustrated, neutral, or happy.

9. The method of claim 1, comprising performing an action when a certain behavior is predicted, wherein the action comprises sounding an alarm, calling emergency services, triggering an alert, sending a message, displaying an alert, or some combination thereof.

10. The method of claim 1, wherein the one or more cameras comprise red, green, blue, depth (RGB+D) cameras that capture estimates of location and articulated body motion, and fixed cameras and pan tilt zoom (PTZ) cameras that capture facial imagery.

11. One or more tangible, non-transitory computer-readable media storing computer instructions that, when executed by one or more processors, cause the one or more processors to:
receive data related to one or more individuals from one or more cameras in an environment;
execute one or more agent based simulators that each model behavior of a respective individual and each output symbolic sequences representative of internal experiences of the respective individual during simulation; and
predict a subsequent behavior for each of the respective individuals when the symbolic sequences match a query symbolic sequence for a query behavior;
wherein each model uses particle filtering and each particle includes recurrent neural networks that iteratively estimates temporal evolution of the symbolic sequences based on the data.

12. The one or more computer-readable media of claim 11, wherein particles that include similar symbolic sequences are allowed to transition to the next iteration to predict a next set of internal symbols of the symbolic sequences.

13. The one or more computer-readable media of claim 11, wherein the recurrent neural networks are used to predict the subsequent behavior based on the symbolic sequences.

14. The one or more computer-readable media of claim 11, wherein the computer instructions, when executed by the processor, cause the one or more processors to perform an action when a certain behavior is predicted, wherein the action comprises sounding an alarm, calling emergency services, triggering an alert, sending a message, displaying an alert, or some combination thereof.

15. A system, comprising:
one or more cameras that capture data related to a behavior of one or more individuals in an environment;
one or more computing devices comprising one or more processors that:
receive the data related to the behavior of one or more individuals from one or more cameras in an environment;
execute one or more agent based simulators that each model the behavior of a respective individual and each output symbolic sequences representative of internal experiences of the respective individual during simulation; and
predict a subsequent behavior for each of the respective individuals when the symbolic sequences match a query symbolic sequence for a query behavior; and
a display coupled to the one or more computing devices and configured to display an indication representative of the subsequent behavior;
wherein each model uses particle filtering and each particle includes recurrent neural networks that iteratively estimates temporal evolution of the symbolic sequences based on the data.

16. The system of claim 15, wherein the one or more cameras comprise red, green, blue, depth (RGB+D) cameras that capture estimates of location and articulated body motion, and fixed cameras and pan tilt zoom (PTZ) cameras that capture facial imagery.

17. The system of claim 15, wherein the one or more computing devices comprise a smartphone, a smartwatch, a tablet, a laptop computer, a desktop computer, a server in a cloud-based computing system, or some combination thereof.

18. The system of claim 15, wherein the one or more processors perform an action when a certain subsequent behavior is predicted, the action comprising sounding an alarm, calling emergency services, triggering an alert, sending a message, displaying an alert, or some combination thereof.

* * * * *